(12) United States Patent
Jilesen et al.

(10) Patent No.: US 12,125,596 B2
(45) Date of Patent: Oct. 22, 2024

(54) COMPUTER SIMULATION OF HUMAN RESPIRATORY DROPLETS

(71) Applicant: Dassault Systemes Americas Corp., Waltham, MA (US)

(72) Inventors: Jonathan T. Jilesen, Waltham, MA (US); Gregory M. Laskowski, Waltham, MA (US)

(73) Assignee: Dassault Systemes Americas Corp., Waltham, MA (US)

( * ) Notice: Subject to any disclaimer, the term of this patent is extended or adjusted under 35 U.S.C. 154(b) by 270 days.

(21) Appl. No.: 17/131,905

(22) Filed: Dec. 23, 2020

(65) Prior Publication Data

US 2022/0199261 A1 Jun. 23, 2022

(51) Int. Cl.
*G16H 50/50* (2018.01)
*G06F 30/25* (2020.01)

(52) U.S. Cl.
CPC .............. *G16H 50/50* (2018.01); *G06F 30/25* (2020.01)

(58) Field of Classification Search
CPC ................................ G06F 30/25; G16H 50/50
See application file for complete search history.

(56) References Cited

U.S. PATENT DOCUMENTS

| 2013/0151221 A1 | 6/2013 | Chen et al. | |
| 2022/0138347 A1* | 5/2022 | McDonagh | G06Q 10/10 |
| | | | 705/2 |

OTHER PUBLICATIONS

Gupte et al., "Flow dynamics and characterization of a cough," Indoor Air, Dec. 2009, 19(6):517-525.
"Respiratory tract," https://en.wikipedia.org/wiki/Respiratory_tract, this page was last edited on Dec. 14, 2020, p. 1-4.
Extended European Search Report in European Appln No. 21212475. 4, dated May 17, 2022, 12 pages.
Hamidreza et al., "In Silico Investigation of Sneezing in a Full Real Human Upper Airway Using Computational Fluid Dynamics Method," Computer Methods and Programs in Biomedicine, Aug. 1, 2019.
Hoffman et., "Computational Modelling of Cough Function and Airway Penetrant Behavior in Patients with Disorders of Laryngeal Function: Disorders of Laryngeal Function," Laryngoscope Investigative Otolaryngology, Jan. 31, 2017, 2(1):23-29.

* cited by examiner

*Primary Examiner* — Bijan Mapar
(74) *Attorney, Agent, or Firm* — Fish & Richardson P.C.

(57) ABSTRACT

Described are computer aided techniques to simulate a human respiratory event. The computer aided techniques access a model including a portion of a person's respiratory tract, which models the respiratory tract as a volumetric region, initiate a respiratory event into the volumetric regions, which respiratory event originates in the accessed model at a depth that is inside of the modeled respiratory tract, simulate movement of elements of the respiratory event within the volumetric region, with the elements representing particles of the respiratory event, at an inlet boundary condition representing an area of the model that is at the threshold depth inside the respiratory tract, and obtain from the simulation, a representation of a trajectory of particles of the respiratory event.

17 Claims, 16 Drawing Sheets

COMPUTER SIMULATION OF HUMAN RESPIRATORY DROPLETS

BACKGROUND

Human respirator droplets are emitted when humans breathe, talk, sing, cough, sneeze, etc. The ability to predict how these particles disperse into the surrounding environment is helpful for producing guidance for social distancing, making design changes to improve air quality and reduce risk of infection, as well as, for producing effective personal protective equipment.

SUMMARY

According to an aspect, a computer implemented method performed by one or more computer systems includes accessing a model including a portion of a person's respiratory tract, which models the respiratory tract as a volumetric region, initiating a respiratory event into the volumetric regions, which respiratory event originates in the accessed model at a depth that is inside of the modeled respiratory tract, simulating movement of elements of the respiratory event within the volumetric region, with the elements representing particles of the respiratory event, at an inlet boundary condition representing an area of the model that is at the threshold depth inside the respiratory tract, and obtaining from the simulating, a representation of a trajectory of particles of the respiratory event.

Embodiments of the computer implemented method may include any one or more of the following features or other features disclosed herein.

The representation of the respiratory tract includes a model of the pharynx. The representation of the respiratory tract includes a model of the oropharynx region of the pharynx. Initiating occurs at a region that represents the oropharynx region of the pharynx, with simulating further including simulating fluid flow of the respiratory event from the oropharynx region of the pharynx through the oral cavity and out of the mouth of a person. Initiating occurs at a region that represents the laryngopharynx region of the pharynx, with simulating further including simulating fluid flow of the respiratory event from the laryngopharynx region of the pharynx through the oropharynx region, the oral cavity, and out of the mouth of a person. The simulated respiratory event is a cough.

According to an additional aspect, a computer system includes one or more processor devices, memory coupled to the one or more processor devices, storage storing executable computer instructions for conducting a fluid simulation of a human respiratory event, the instructions to configure the one or more processors to access a model including a portion of a person's respiratory tract, which models the respiratory tract as a volumetric region, initiate a respiratory event into the volumetric regions, which respiratory event originates in the accessed model at a depth that is inside of the modeled respiratory tract, simulate movement of elements of the respiratory event within the volumetric region, with the elements representing particles of the respiratory event, at an inlet boundary condition representing an area of the model that is at the threshold depth inside the respiratory tract, and obtain from the simulation, a representation of a trajectory of particles of the respiratory event.

Embodiments of the computer system may include any one or more of the following features or other features disclosed herein.

The representation of the respiratory tract includes a model of the pharynx. The representation of the respiratory tract includes a model of the oropharynx region of the pharynx. Initiate occurs at a region that represents the oropharynx region of the pharynx, with instructions to simulate further including instructions to simulate fluid flow of the respiratory event from the oropharynx region of the pharynx through the oral cavity and out of the mouth of a person. The system is further configured to initiate at a region that represents the laryngopharynx region of the pharynx, with simulate further configured to simulate fluid flow of the respiratory event from the laryngopharynx region of the pharynx through the oropharynx region, the oral cavity, and out of the mouth of a person. The respiratory event is a cough.

According to an additional aspect, a computer program product tangibly stored on a computer readable non-transitory storage device that stores executable computer instructions to simulate a human respiratory event, the instructions for causing a computing system to access a model including a portion of a person's respiratory tract, which models the respiratory tract as a volumetric region, initiate a respiratory event into the volumetric regions, which respiratory event originates in the accessed model at a depth that is inside of the modeled respiratory tract, simulate movement of elements of the respiratory event within the volumetric region, with the elements representing particles of the respiratory event, at an inlet boundary condition representing an area of the model that is at the threshold depth inside the respiratory tract, and obtain from the simulation, a representation of a trajectory of particles of the respiratory event.

Embodiments of the computer program product may include any one or more of the following features or other features disclosed herein.

The representation of the respiratory tract includes a model of the pharynx. The representation of the respiratory tract includes a model of the oropharynx region of the pharynx. The instructions to initiate occurs at a region that represents the oropharynx region of the pharynx, with the instructions further including instructions to simulate fluid flow of the respiratory event from the oropharynx region of the pharynx through the oral cavity and out of the mouth of a person. The instructions further include instructions to initiate at a region that represents the laryngopharynx region of the pharynx, with instructions to simulate further including instructions to simulate fluid flow of the respiratory event from the laryngopharynx region of the pharynx through the oropharynx region, the oral cavity, and out of the mouth of a person. The simulated respiratory event is a cough.

One or more of the above aspects may provide one or more of the following advantages.

Simulation according to the above approach provides realistic respirator droplet clouds produced by the simulation. These clouds are much more dispersed and representative of experimentally imaged respirator clouds than those of other methods. Other methods tend to under predict the dispersion of the droplets. By having the inlet boundary condition inside the throat we do not need to set cone angles or introduce artificial turbulence based on experimental results in order to achieve a realistic cough. In fact these characteristics become metrics by which we can verify we are accurately simulating the respiratory event.

The above approach is applicable to Lattice Boltzmann Method, as well as other computational fluid-dynamics methods including finite-volume method, finite-element method, etc.

Other features and advantages of the invention will become apparent from the following description, and from the claims.

DETAILED DESCRIPTION

Figure 1:
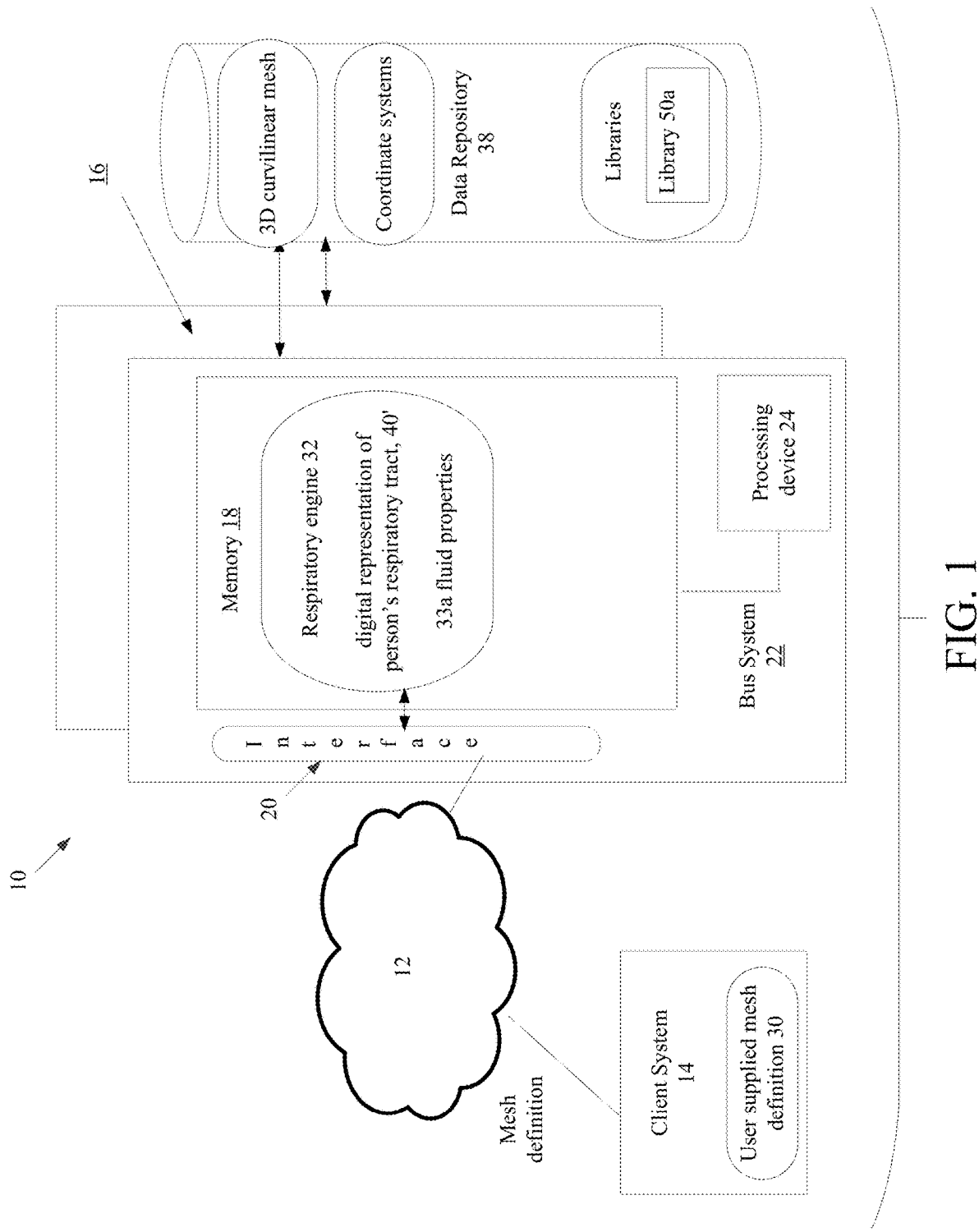
FIG. 1 depicts a system for simulation of a respiratory event.

Referring to FIG. 1, a system 10 for conducting a simulation of a respiratory event is shown. The simulation can be for various purposes such as to produce guidance materials for social distancing, producing design changes to improve air quality, and reduce risk of infection, as well as, for producing effective personal protective equipment. The focus of the discussion herein will be on simulation of a cough, as the respiratory event. The simulation of the cough is initiated at a location within a person's respiratory tract.

In general, the system 10 in this implementation is based on a client-server or cloud based architecture and includes a server system 12 implemented as a massively parallel computing system 12 (stand alone or cloud-based) and a client system 14. The server system 12 includes memory 18, a bus system 11, interfaces 20 (e.g., user interfaces/network interfaces/display or monitor interfaces, etc.) and a processing device 24.

Figure 2:
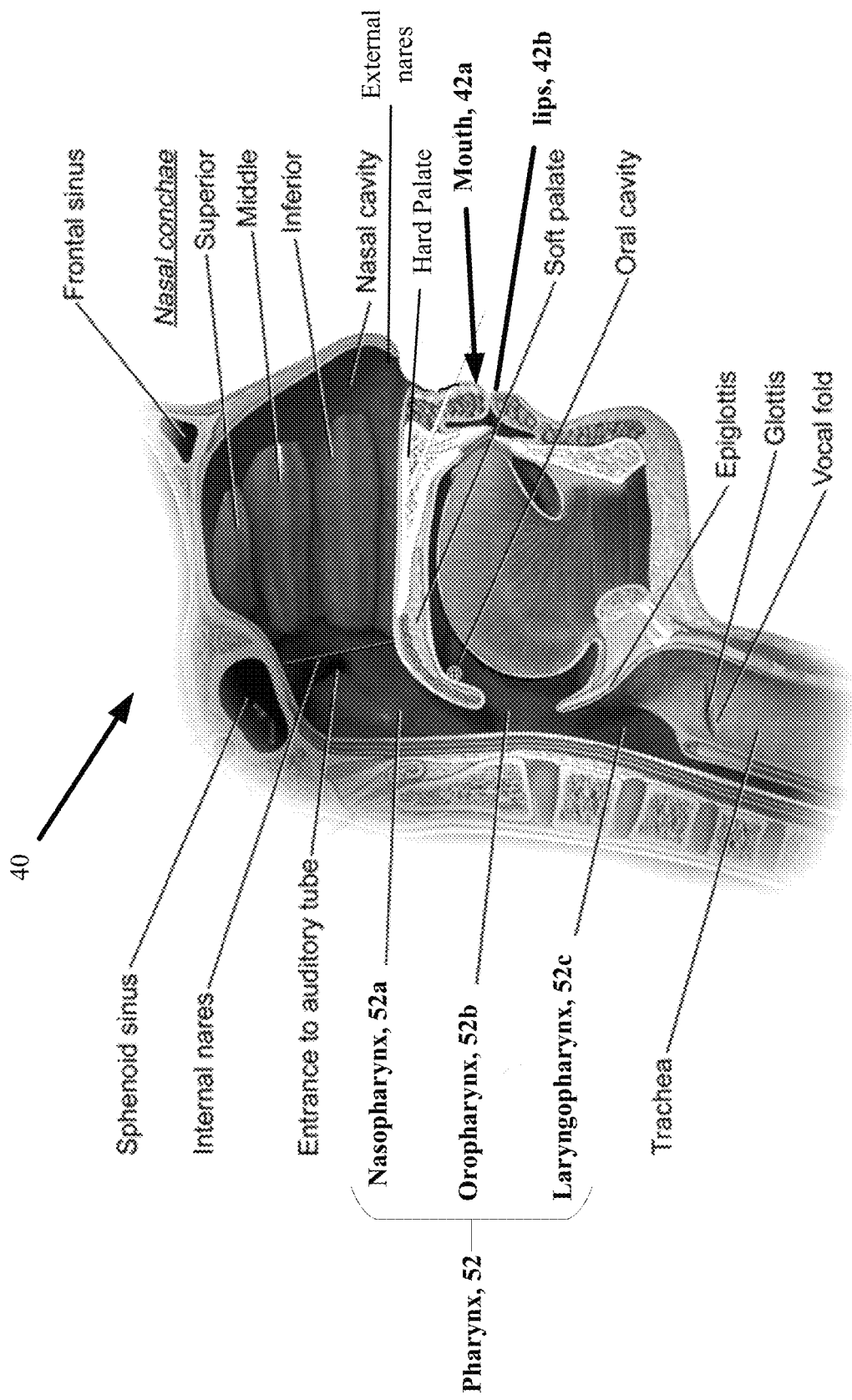
FIG. 2 is an image that depicts aspects of a person's upper respiratory tract.

For the example of a cough simulation, in memory 18 are a respiratory engine 32 that operates on a digital representation 40' of a person's respiratory tract 40 (FIG. 2) that digitally represents various spaces and objects in the respiratory tract 40 (FIG. 2). The digital representation 40' of the user's respiratory tract 40 (FIG. 2) also includes the person's throat. The digital representation 40' of the user's respiratory tract 40 (FIG. 2) includes the person's throat which includes the nasopharynx, the oropharynx and the laryngopharynx sections of the throat (see FIG. 2, below). The system 10 requires the digital representation 40' of the person's respiratory tract 40 (FIG. 2) to include the mouth portion and the throat portion of the person's respiratory tract. Within the throat portion of the person's respiratory tract 40 (FIG. 2) is a boundary condition for initiating the respiratory event, e.g., a cough.

One approach to providing the digital representation 40' of the person's respiratory tract is to obtain the digital representation 40' from a third-party generated model.

The memory 18 may also store other parameters such as fluid properties 33a, e.g., fluid, (e.g., saliva) properties of the mouth that covers various objects within the mouth. The memory 18 also stores parameters such as mucous membranes that secret mucous.

The system 10 accesses a data repository 38 that stores 2D and/or 3D meshes, coordinate systems, and libraries that can be used for respiratory event simulations using any well-known computational technique such as computational fluid dynamics or the so called Lattice Boltzmann method.

The respiratory engine 32 initiates a cough, i.e., a respiratory event, within the throat e.g., the pharynx portion of the respiratory tract. In one embodiment, the pharynx portions are limited to the oropharynx and the laryngopharynx sections of pharynx. In other embodiments, the nasopharynx section of the pharynx may be used to simulate a sneeze and/or cough.

Referring momentarily to FIG. 2, a depiction of the person's upper respiratory tract 40 is shown. The depiction was adapted from an image found at https://en.wikipedia.org/wiki/Respiratory_tract. The depiction of the person's respiratory track 40 is representative of a live person. The representation 40 is converted into a digital representation of the person's tract 40' that will be used to conduct a simulation. The major objects in the person's respiratory tract 40 are labeled by name. Of these major objects, some of these objects are labeled by name and a reference, and include the mouth 42a and lips 42a. Also shown are other major objects, labeled by name and a reference, and include the throat e.g., the pharynx 52 that includes the nasopharynx 52, the oropharynx 52b, and the laryngopharynx 52c. Other portions of the upper respiratory tract 40 include the hard palate, soft palate, teeth (not labeled), fluid membranes, oral cavity including at least the oral cavity proper and may include the vestibule portion (not labeled) of the oral cavity.

Figure 3:
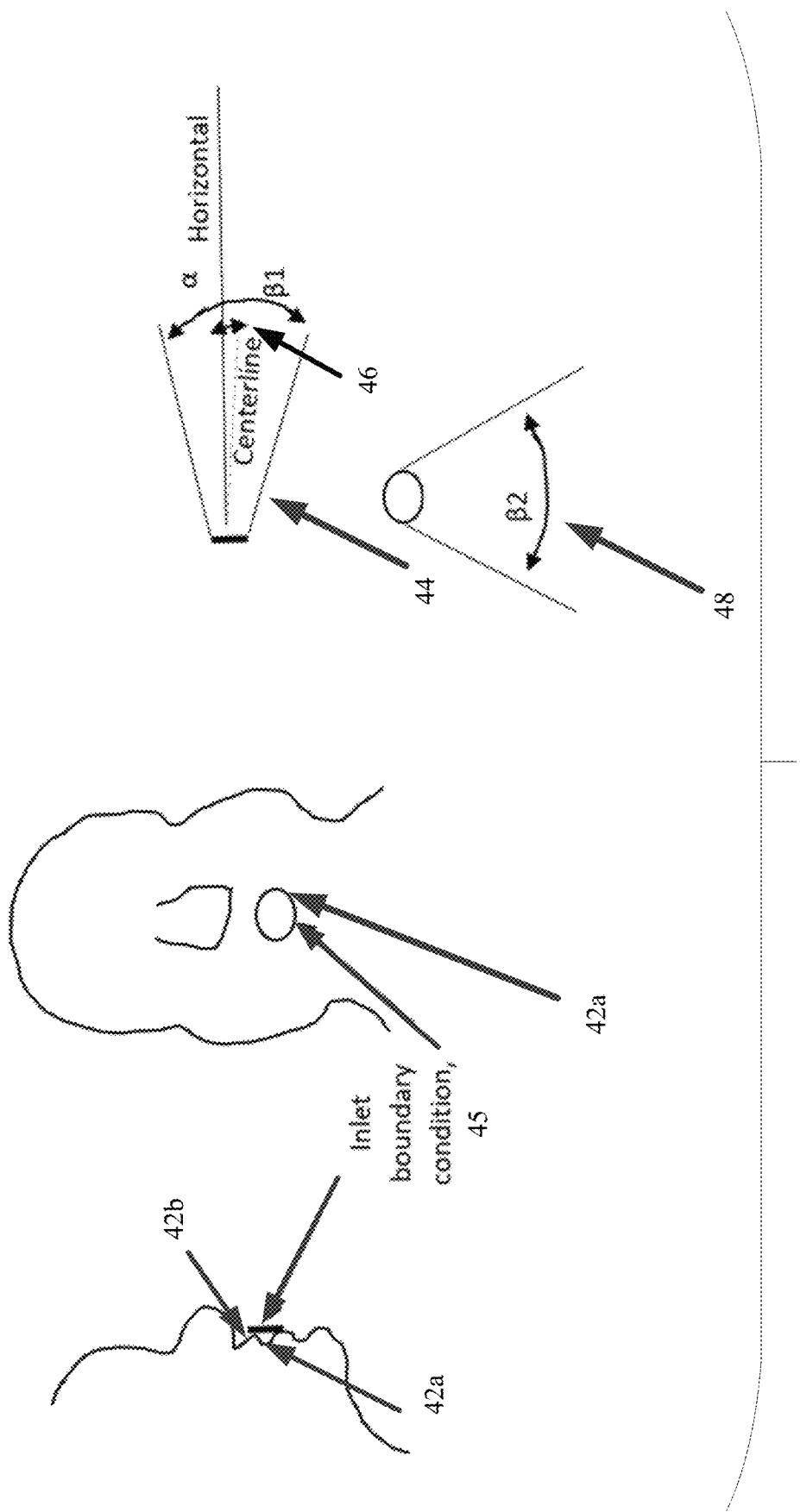
FIG. 3 depicts conventional modeling of the respiratory event.

Referring now to FIG. 3, conventionally, as understood, the simulation event is modeled as occurring at the exit of the mouth 42a of the person 40, e.g., at the lips 42b. That is, the so called inlet boundary condition 45 occurs at the mouth exit, e. g. at the lips 42b of the person. Conventionally, therefore a user of the system 10 would need to set cone angles 44 ($\alpha$) and cone angles 46 ($\beta_1$) and 48 ($\beta_2$), and introduce artificial turbulence based on experimental results in order to achieve a simulation of a realistic cough. Typically a cough setup has an oval or sphere section as inlet boundary condition 45. This inlet is positioned just in front or inside the mouth opening, as shown. The user specifies the angles, $\alpha$, $\beta1$, $\beta2$ for the inlet boundary condition to achieve the desired cone shape. This can be done by varying inlet velocity conditions or through control of the radius and solid angle of the spherical section used for the inlet geometry. For higher fidelity simulations, artificial turbulence needs to be introduced to create the structures of the cough. This is often neglected however. (See a paper entitled: "Flow Dynamics and Characterization of a Cough" by Jitendra K.

Gupta et al. published at Indoor Air, 19, 517-525 (2009) incorporated herein by reference).

Figure 4:
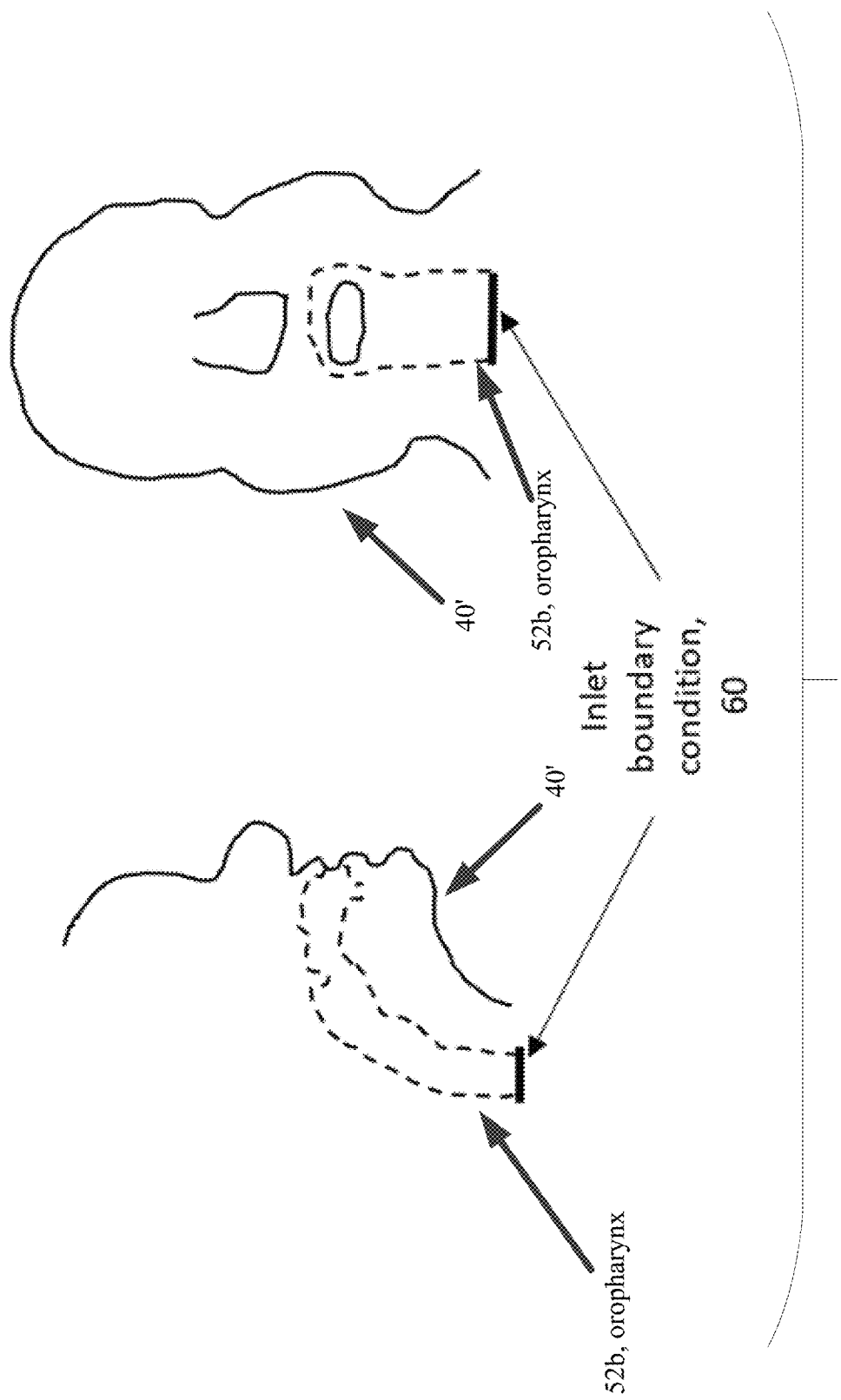
FIG. 4 depicts an alternative technique for modeling of a respiratory event.

Referring now to FIG. 4, the simulation event as used herein, e.g., a cough, is modeled as originating within the throat or pharynx 52 of the person. More specifically, the simulation engine 34 initiates the cough as modeled from a portion of the person's throat that is at least at an exit of the oropharynx 52b, e.g. around the corner at the back of the oral cavity to get correct flow development. In some implementations, initiation of the cough occur at an entrance of the oropharynx 52b or an entrance of the laryngopharynx 52c of the pharynx 52. In terms of a computer generated simulation, the point of initiation of the cough is the so called "boundary condition, 60."

By moving the inlet boundary condition 55 from the mouth to the inlet boundary condition 60 that is into the throat 52, there is no longer any need to specify, specific cone angles or solid angles for at the inlet. The inlet becomes a mass flow inlet boundary condition. Also, there is no longer any need to introduce artificial turbulence as the simulated flow through the throat and mouth geometry produces these structures. Therefore, angles α, β1, and β2, as specified in the above paper, now become results of the simulation and can be used to validate the results of the cough.

The boundary condition 60 for the cough that is deep inside the respiratory track is so that turbulent structures of a fluid flow develop naturally during the simulation. This gives the cough structures more realistic intensities and length scales than if they were generated artificially.

A high fidelity flow simulation such as PowerFLOW available from Dassault Systems SIMUOLIA Corp. can be used to capture the development of these cough structures. The correct modeling of these cough structures improves the accuracy of the dispersion of the respiratory droplets into the environment.

Figure 5:
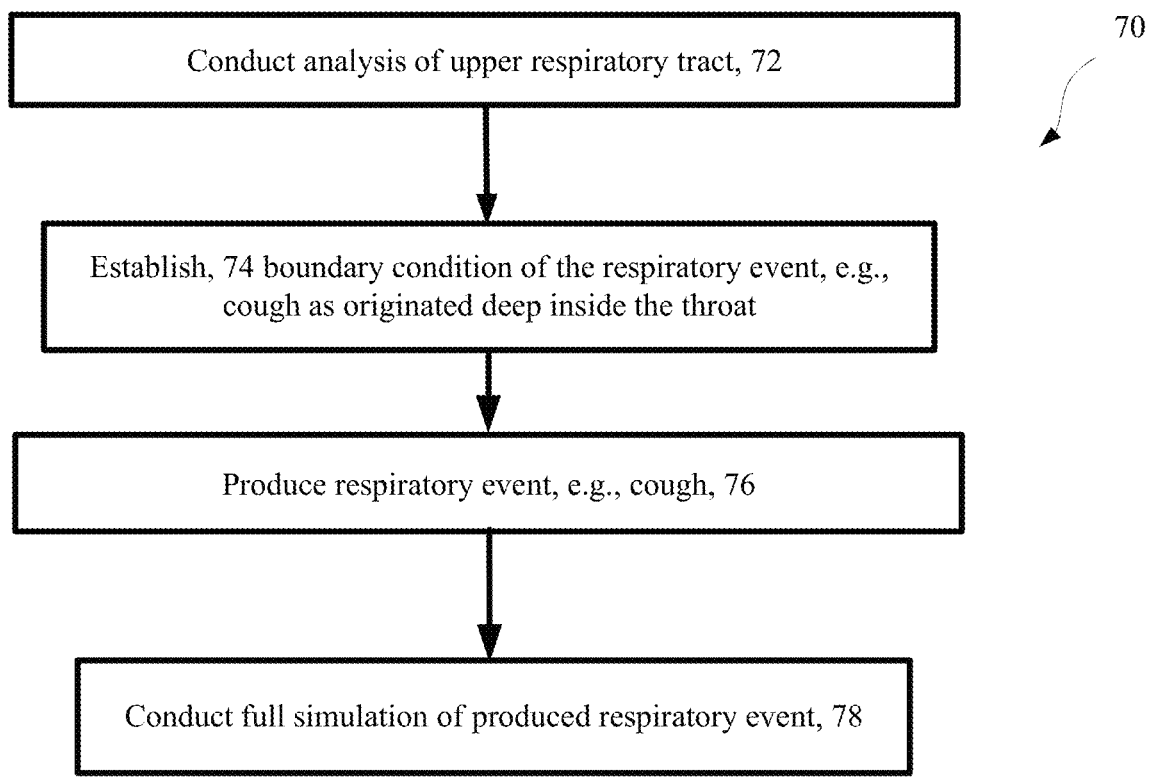
FIG. 5 depicts a flow diagram of a process for modeling the respiratory event of FIG. 4.

Referring now to FIG. 5, a process 70 for conducting a multi-component fluid-flow simulation for a respiratory event that originates at least at an entrance to the oropharynx 52b is shown. The process 70, uses a simulation of a upper respiratory tract of a person as an example. Process 70 includes conducting 72 a geometrical analysis of a typical upper respiratory tract, using X-ray or other types of images to identify various objects that are to be modeled in the upper respiratory tract being studied.

The simulation engine produces 76 a respiratory event by combining exhalation rate profiles, particle distribution sizes and concentration data. One example is to obtain these data from the literature. These data are used to approximate the respirator event.

A decision about where to place the boundary condition for the introduction of the particles and the airflow, when guided by conventional literature provides histograms of the particle size distributions, the timing at which these different size particles are emitted is not specified. Furthermore the initial velocity of the particles is not specified. Concentration data available from literature is also averaged data and does not include information on the time variation of the respirator droplets during the event.

The methodology described herein establishes 74 the boundary condition for the simulation of the cough as originated deep inside the throat in the region of the oropharynx or beyond. The need for the inlet to be so deep inside the respiratory track is so that the turbulent structures of the flow through the remainder of the upper respiratory tract develop naturally, according to the model of the respiratory tract. This gives the structure of the cough a more realistic intensity and length scales than if generated artificially.

Upon producing of the respiratory event, the process conducts a full simulation of the produced event, by propagating the event through the model of the upper respiratory tract of the person 40.

Figure 6:
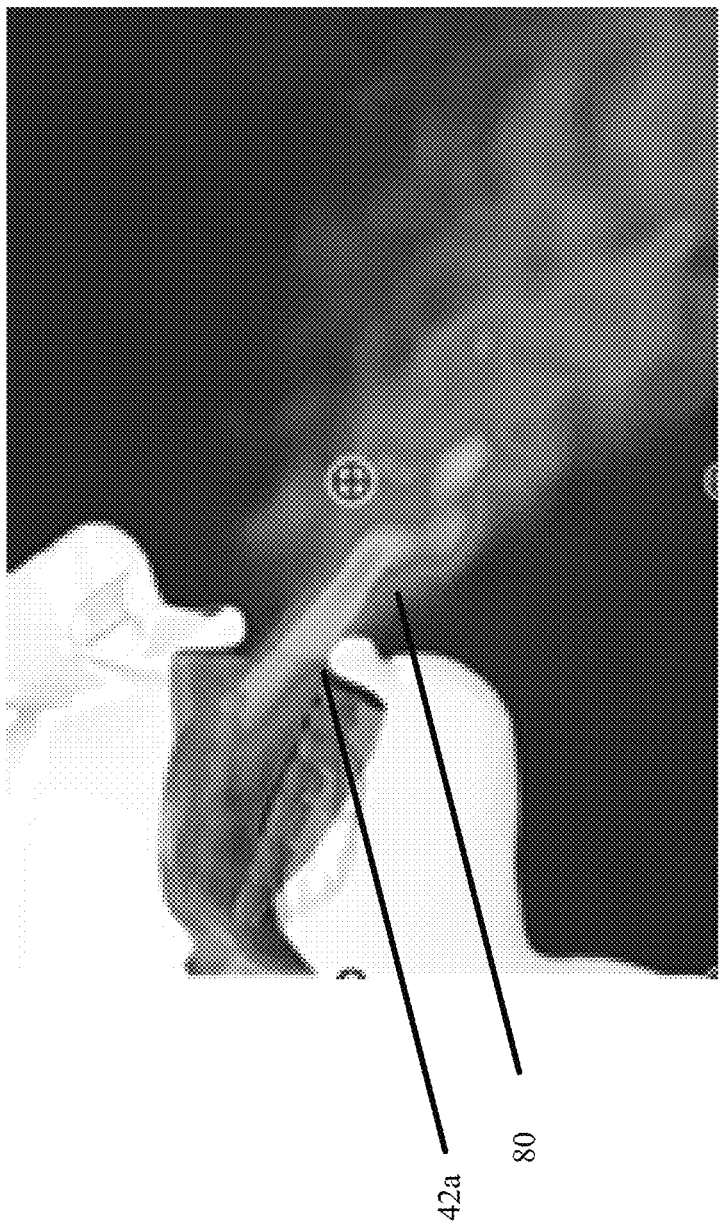
FIGS. 6 and 7 depict aspects of a simulated cough.

FIG. 6 depicts a velocity slice 80 of the cough that originates in the oropharynx, produced by process 76, which shows an example of how the resulting flow interacts with the features of the mouth to develop the cough jet output from the mouth 42a.

Figure 7:
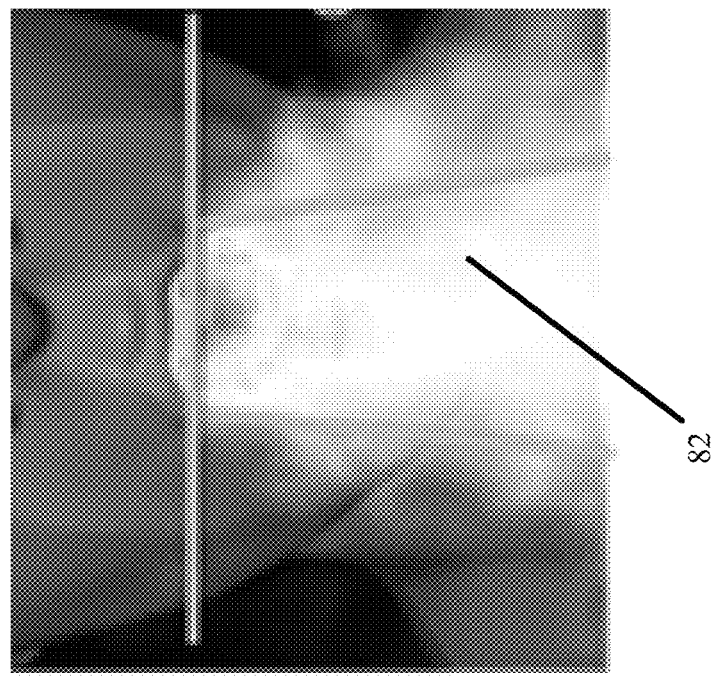
Figure 7:
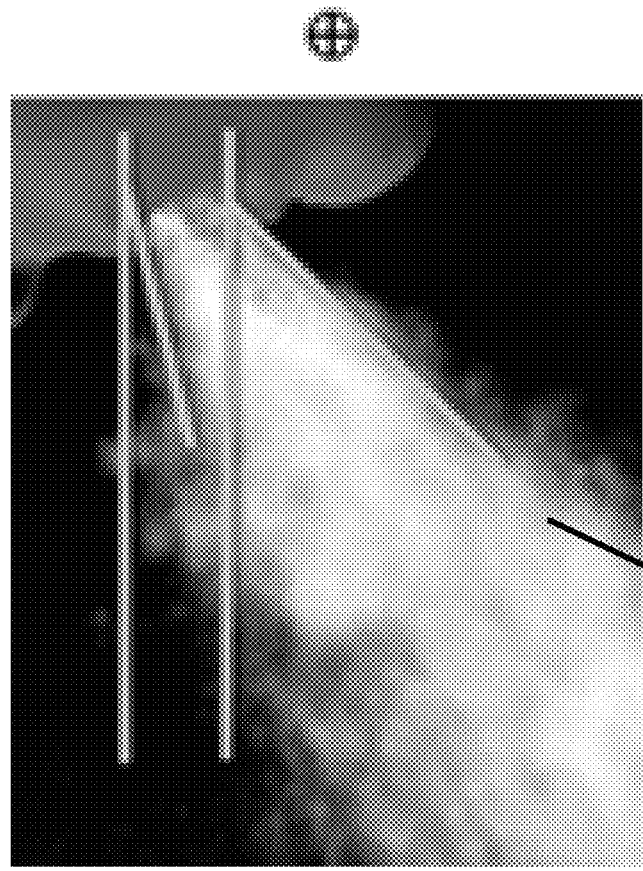

FIG. 7 depicts a volumetric visualization of droplet concentration 82, showing how the cough jet disperses the particles.

These images are compared with results shown in Gupta, J., Lin, C.-H., and Chen, Q. 2009. "Flow dynamics and characterization of a cough," Indoor Air, 19, 517-525.

Thermal considerations are also included with the breath being introduced at a temperature higher than ambient and close to the internal temperature of the subject. The particle size distribution used in the model is a Normal Distribution fitted to the diameter data of Zayas et al. (2012), which is centered around 0.3 µm. This distribution was chosen as it captures smaller particles than other previous experiments due to improvements in measurement techniques.

Figure 8:
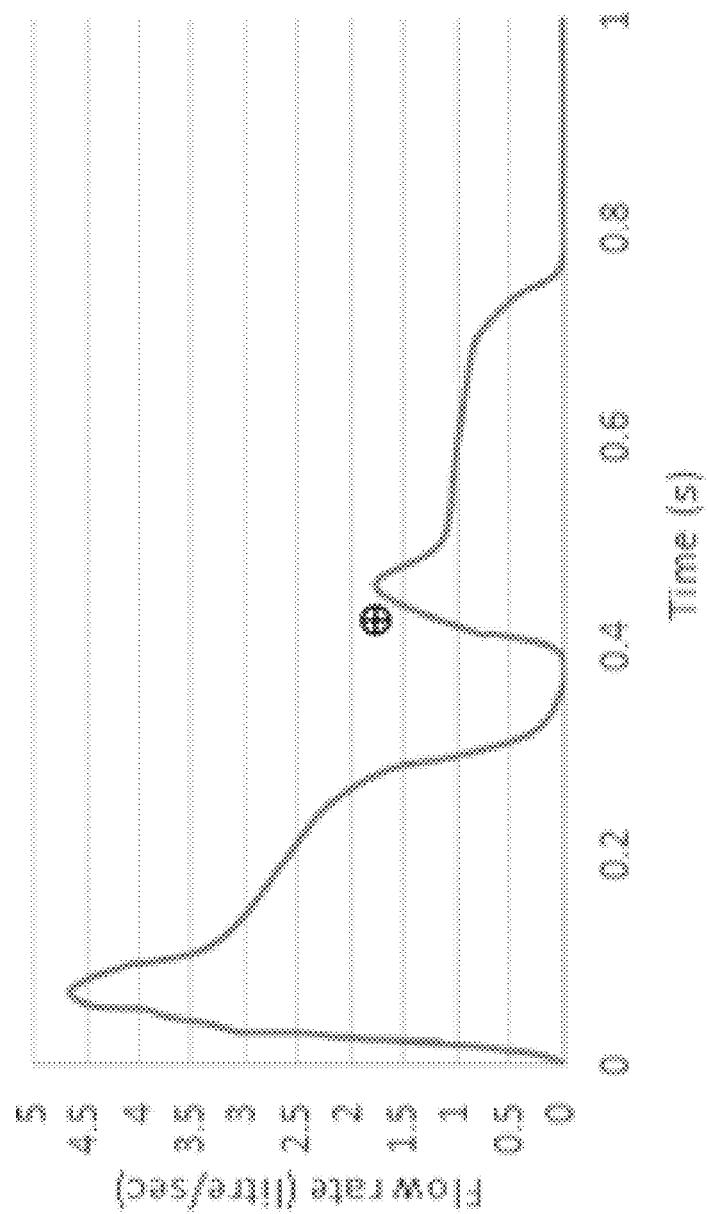
FIG. 8 is a graph that depicts a relationship of cough flow rate v. time.

As shown in FIG. 8, the cough can be a double cough with the flow rate variation over time taken from Gupta, Lin & Chen (2009).

A simulation example is explained in the discussion below. FIGS. 9, 10 and 12-16 are labeled as "prior art," because these figures are found in other applications/patents of the assignee. However, the discussion above, is not found in those applications. The discussion below is one way of simulating the cough event. Other simulation techniques could be used.

Figure 9:
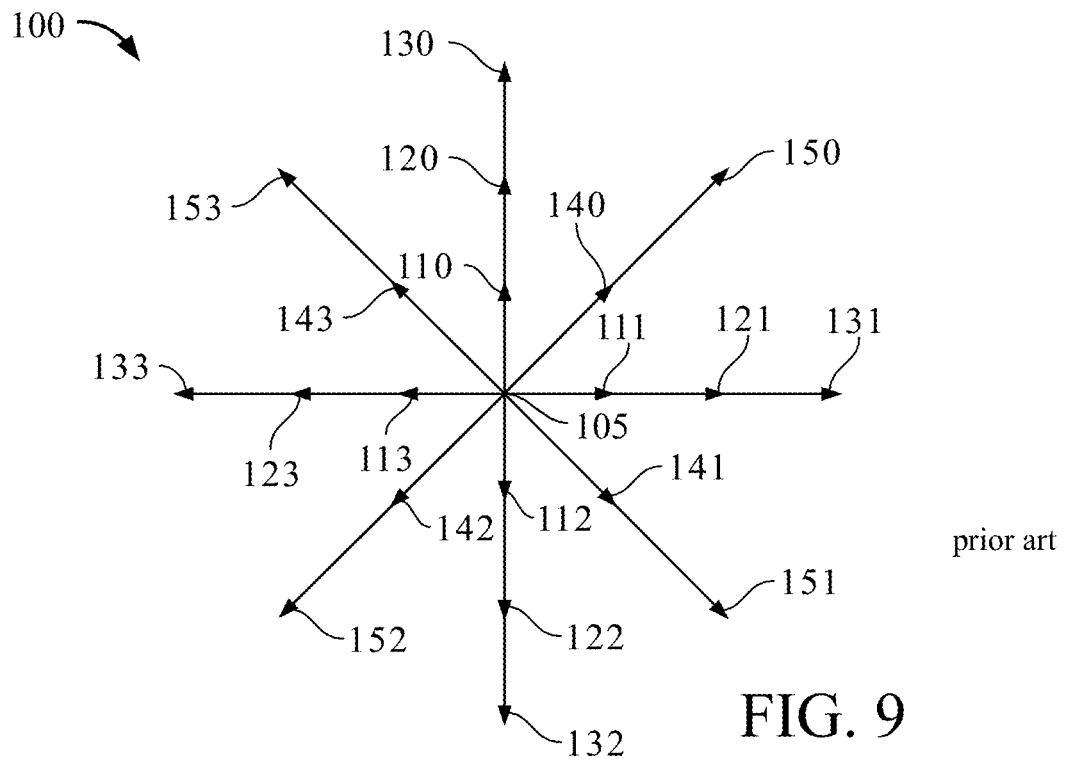
FIGS. 9 and 10 illustrate velocity components of two LBM models (prior art).

Referring to FIG. 9, a first model (2D-1) 100 is a two-dimensional model that includes 21 velocities. Of these 21 velocities, one (105) represents particles that are not moving; three sets of four velocities represent particles that are moving at either a normalized speed (r) (110-113), twice the normalized speed (2r) (120-123), or three times the normalized speed (3r) (130-133) in either the positive or negative direction along either the x or y axis of the lattice; and two sets of four velocities represent particles that are moving at the normalized speed (r) (140-143) or twice the normalized speed (2r) (150-153) relative to both of the x and y lattice axes.

Figure 10:
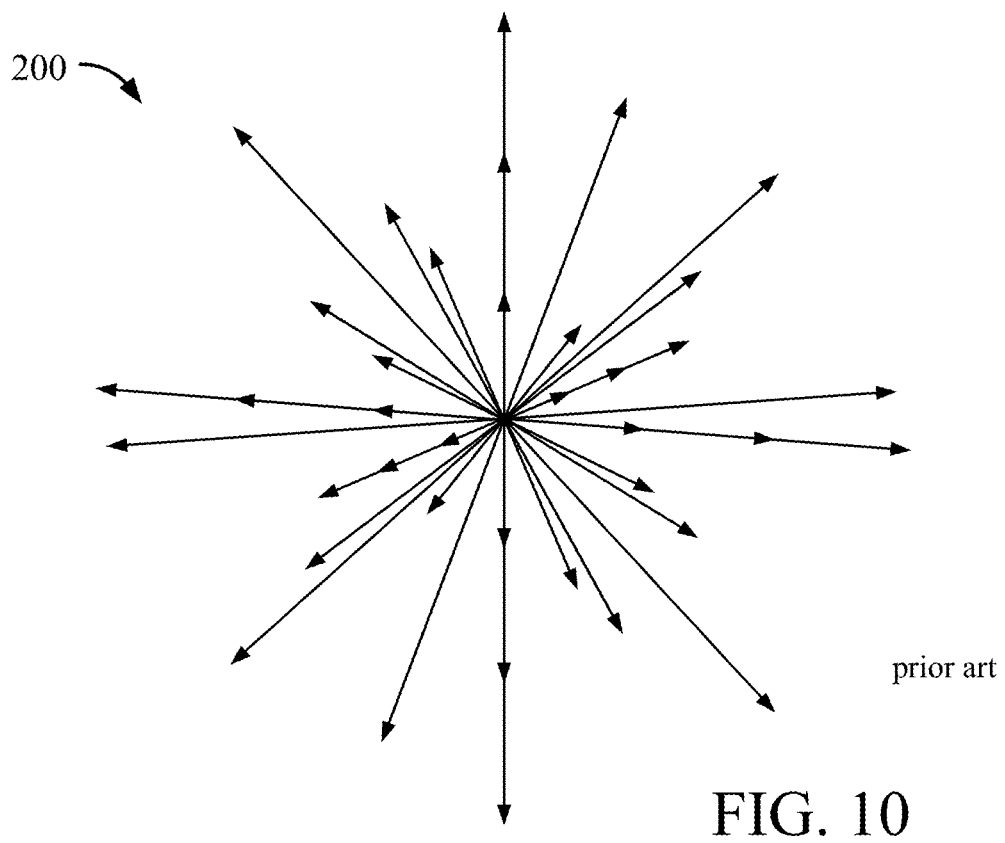

As also illustrated in FIG. 10, a second model (3D-1) 200 is a three-dimensional model that includes 39 velocities, where each velocity is represented by one of the arrowheads of FIG. 8. Of these 39 velocities, one represents particles that are not moving; three sets of six velocities represent particles that are moving at either a normalized speed (r), twice the normalized speed (2r), or three times the normalized speed (3r) in either the positive or negative direction along the x, y or z axis of the lattice; eight represent particles that are moving at the normalized speed (r) relative to all three of the x, y, z lattice axes; and twelve represent particles that are moving at twice the normalized speed (2r) relative to two of the x, y, z lattice axes.

More complex models, such as a 3D-2 model includes 101 velocities and a 2D-2 model includes 37 velocities also may be used. The velocities are more clearly described by their component along each axis as documented in Tables 1 and 2 respectively.

For the three-dimensional model 3D-2, of the 101 velocities, one represents particles that are not moving (Group 1); three sets of six velocities represent particles that are moving at either a normalized speed (r), twice the normalized speed (2r), or three times the normalized speed (3r) in either the positive or negative direction along the x, y or z axis of the lattice (Groups 2, 4, and 7); three sets of eight represent particles that are moving at the normalized speed (r), twice the normalized speed (2r), or three times the normalized speed (3r) relative to all three of the x, y, z lattice axes (Groups 3, 8, and 10); twelve represent particles that are moving at twice the normalized speed (2r) relative to two of the x, y, z lattice axes (Group 6); twenty four represent particles that are moving at the normalized speed (r) and twice the normalized speed (2r) relative to two of the x, y, z lattice axes, and not moving relative to the remaining axis (Group 5); and twenty four represent particles that are moving at the normalized speed (r) relative to two of the x, y, z lattice axes and three times the normalized speed (3r) relative to the remaining axis (Group 9).

For the two-dimensional model 2D-2, of the 37 velocities, one represents particles that are not moving (Group 1); three sets of four velocities represent particles that are moving at either a normalized speed (r), twice the normalized speed (2r), or three times the normalized speed (3r) in either the positive or negative direction along either the x or y axis of the lattice (Groups 2, 4, and 7); two sets of four velocities represent particles that are moving at the normalized speed (r) or twice the normalized speed (2r) relative to both of the x and y lattice axes; eight velocities represent particles that are moving at the normalized speed (r) relative to one of the x and y lattice axes and twice the normalized speed (2r) relative to the other axis; and eight velocities represent particles that are moving at the normalized speed (r) relative to one of the x and y lattice axes and three times the normalized speed (3r) relative to the other axis.

The LBM models described above provide a specific class of efficient and robust discrete velocity kinetic models for numerical simulations of flows in both two-and three-dimensions. A model of this kind includes a particular set of discrete velocities and weights associated with those velocities. The velocities coincide with grid points of Cartesian coordinates in velocity space which facilitates accurate and efficient implementation of discrete velocity models, particularly the kind known as the lattice Boltzmann models. Using such models, flows can be simulated with high fidelity.

Figure 11:
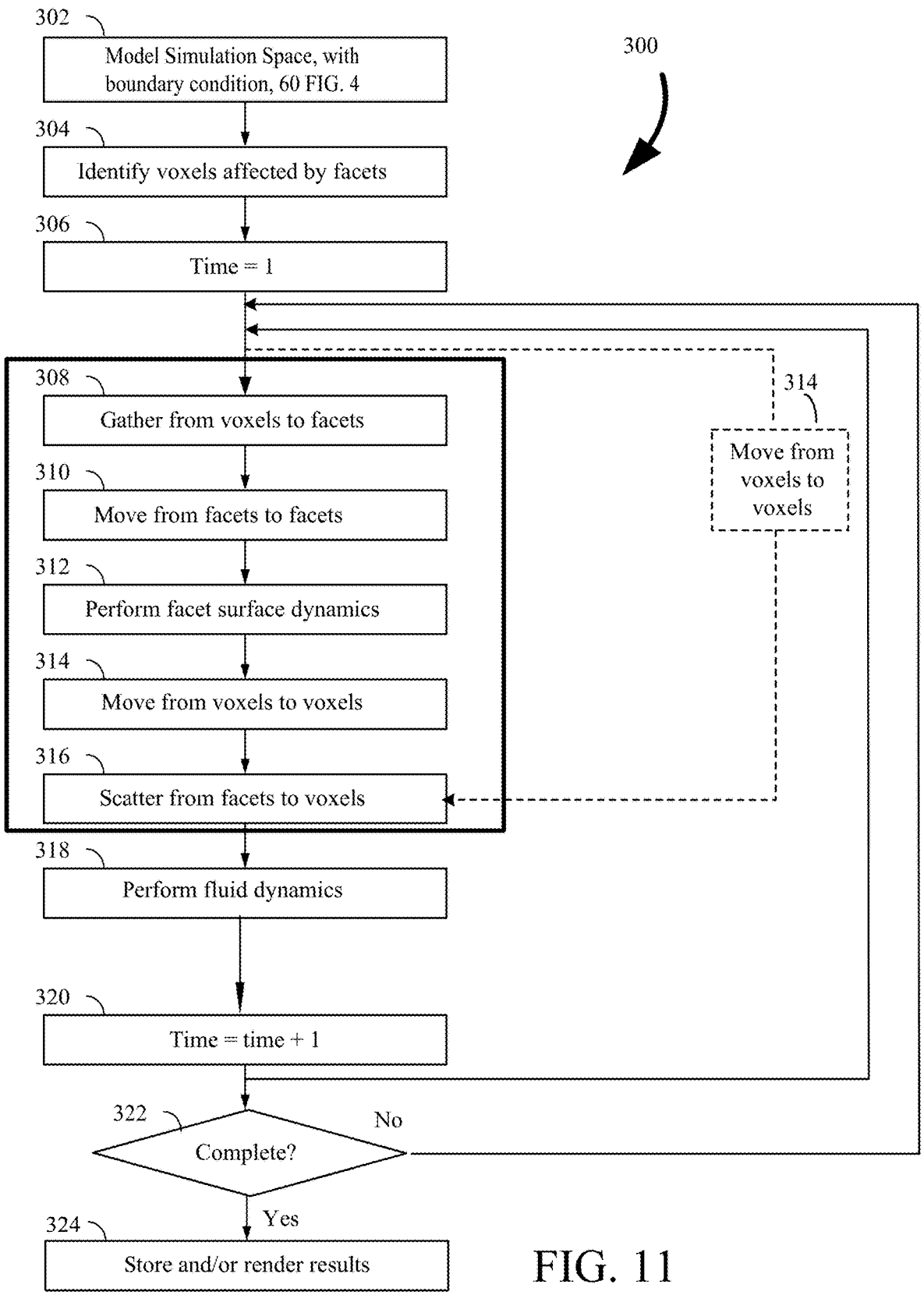
FIG. 11 is a flow chart of a procedure followed by the simulation system of FIG. 1.

Referring to FIG. 11, a physical process simulation system operates according to a procedure 300 to simulate a physical process such as fluid flow that occurs as a result of a cough. Prior to the simulation, a simulation space is modeled using the cough setup of FIG. 4, as a collection of voxels (step 302). Typically, the simulation space is generated using a computer-aided-design (CAD) program. For example, a CAD program could be used to draw a person's upper respiratory track positioned in a room. Thereafter, data produced by the CAD program is processed to add a lattice structure having appropriate resolution and to account for objects and surfaces within the simulation space of the respiratory tract.

The resolution of the lattice may be selected based on the Reynolds number. The Reynolds number is related to the viscosity (v) of the flow, the characteristic length (L) of an object in the flow, and the characteristic velocity (u) of the flow:

$$Re = uL/v.  \qquad \text{Eq.(I-3)}$$

The characteristic length of objects in the respiratory tract is representative of objects found in the tract. The resolution of the simulation event may be increased or areas of increased resolution may be employed around the regions of interest. The dimensions of the voxels decrease as the resolution of the lattice increases.

The state space is represented as $f_i$ (x, t), where $f_i$ represents the number of elements, or particles, per unit volume in state i (i.e., the density of particles in state i) at a lattice site denoted by the three-dimensional vector x at a time t. For a known time increment, the number of particles is referred to simply as $f_i$ (x). The combination of all states of a lattice site is denoted as f(x).

The number of states is determined by the number of possible velocity vectors within each energy level. The velocity vectors consist of integer linear speeds in a space having three dimensions: x, y, and z. The number of states is increased for multiple-species simulations.

Each state i represents a different velocity vector at a specific energy level (i.e., energy level zero, one or two). The velocity $c_i$ of each state is indicated with its "speed" in each of the three dimensions as follows:

$$c_i = (c_{i,x},\ c_{i,y},\ c_{i,z}).  \qquad \text{Eq.(I-4)}$$

The energy level zero state represents stopped particles that are not moving in any dimension, i.e. $c_{stopped} = (0, 0, 0)$. Energy level one states represent particles having a ±1 speed in one of the three dimensions and a zero speed in the other two dimensions. Energy level two states represent particles having either a ±1 speed in all three dimensions, or a ±2 speed in one of the three dimensions and a zero speed in the other two dimensions.

Generating all of the possible permutations of the three energy levels gives a total of 39 possible states (one energy zero state, 6 energy one states, 8 energy three states, 6 energy four states, 12 energy eight states and 6 energy nine states.).

Each voxel (i.e., each lattice site) is represented by a state vector f(x). The state vector completely defines the status of the voxel and includes 39 entries. The 39 entries correspond to the one energy zero state, 6 energy one states, 8 energy three states, 6 energy four states, 12 energy eight states and 6 energy nine states. By using this velocity set, the system can produce Maxwell-Boltzmann statistics for an achieved equilibrium state vector.

Figure 12:
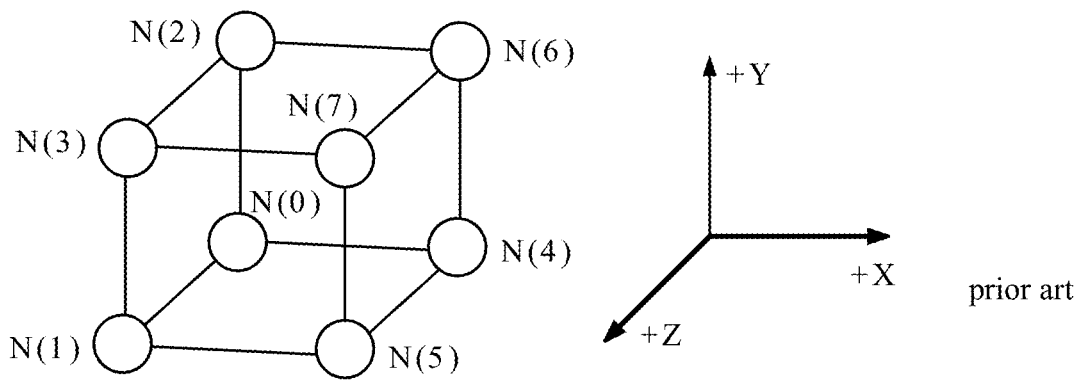
FIG. 12 is a perspective view of a microblock (prior art).

Referring now to FIG. 12, a microblock is illustrated. For processing efficiency, the voxels are grouped in 2×2×2 volumes called microblocks. The microblocks are organized to permit parallel processing of the voxels and to minimize the overhead associated with the data structure. A short-hand notation for the voxels in the microblock is defined as $N_i(n)$, where n represents the relative position of the lattice site within the microblock and n∈{0, 1, 2, . . . , 7}.

Figure 13A:
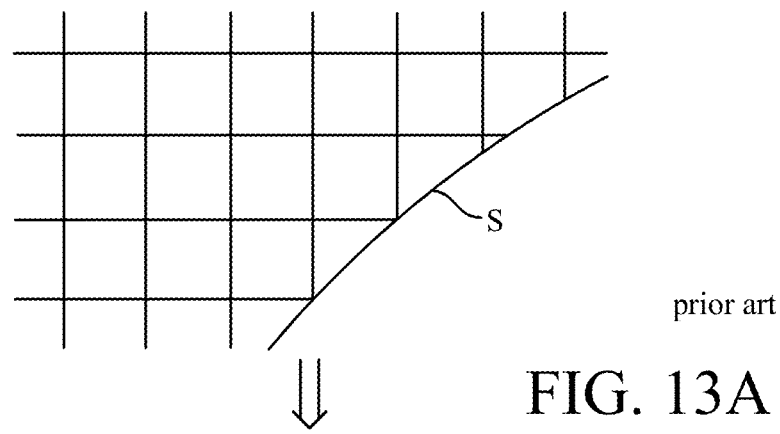
FIGS. 13A and 13B are illustrations of lattice structures (prior art) used by the system of FIG. 1.
Figure 13B:
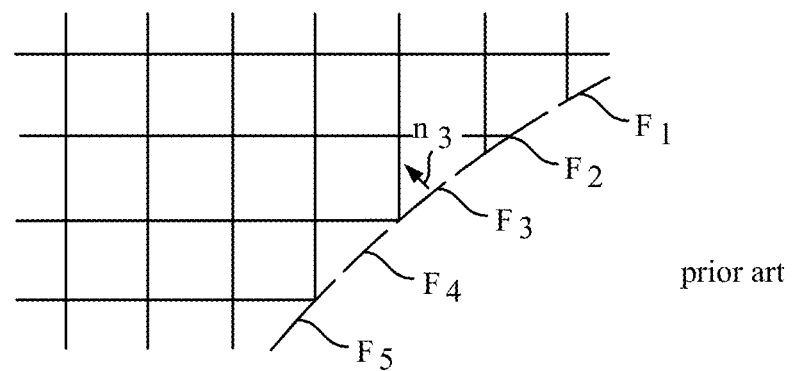

Referring to FIGS. 13A and 13B, a surface S (FIG. 13A) is represented in the simulation space (FIG. 13B) as a collection of facets $F_\alpha$:

$$S = \{F_\alpha\}  \qquad \text{Eq.(I-5)}$$

where α is an index that enumerates a particular facet. A facet is not restricted to the voxel boundaries, but is typically sized on the order of or slightly smaller than the size of the voxels adjacent to the facet so that the facet affects a relatively small number of voxels. Properties are assigned to the facets for the purpose of implementing surface dynamics. In particular, each facet $F_\alpha$ has a unit normal ($n_\alpha$), a surface area ($A_\alpha$), a center location ($x_\alpha$), and a facet distribution function ($f_i(\alpha)$) that describes the surface dynamic properties of the facet.

Figure 14:
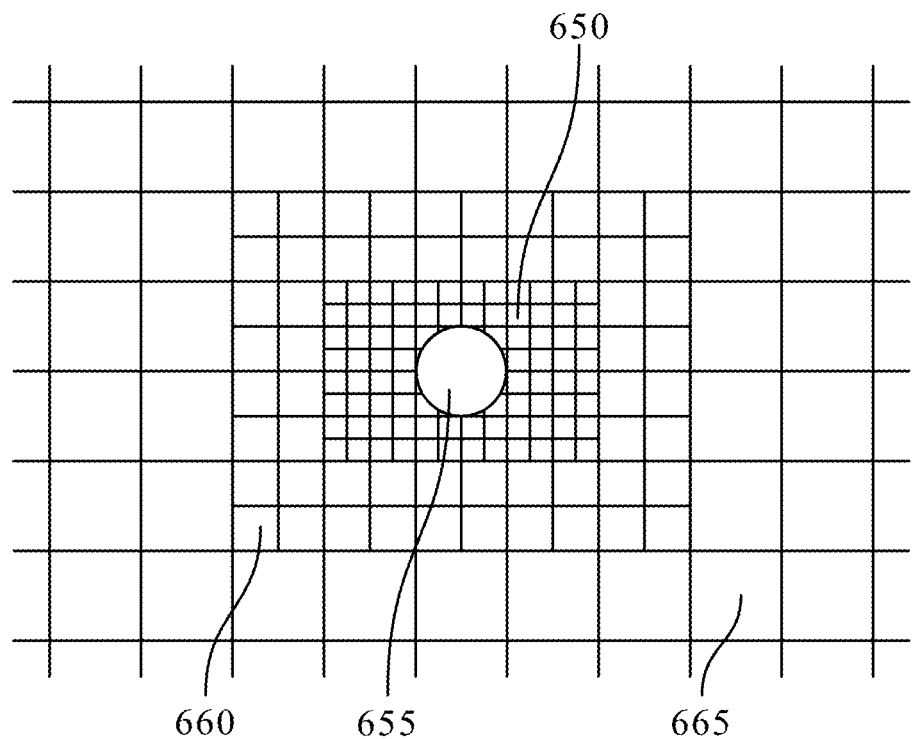
FIGS. 14 and 15 illustrate variable resolution techniques (prior art).

Referring to FIG. 14, different levels of resolution may be used in different regions of the simulation space to improve processing efficiency. Typically, the region 650 around an object 655 is of the most interest and is therefore simulated with the highest resolution. Because the effect of viscosity decreases with distance from the object, decreasing levels of resolution (i.e., expanded voxel volumes) are employed to simulate regions 660, 665 that are spaced at increasing distances from the object 655.

Figure 15:
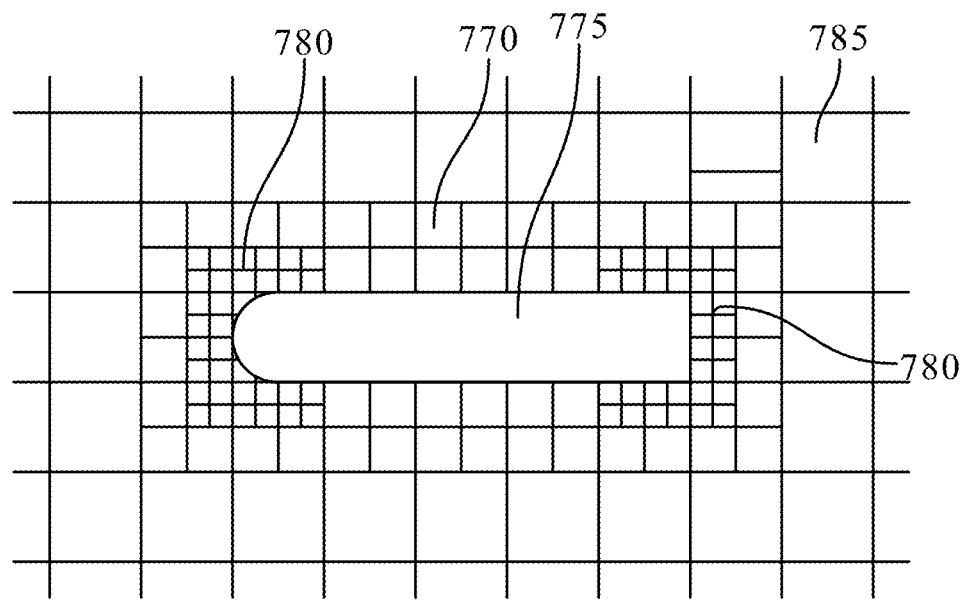

Similarly, as illustrated in FIG. 15, a lower level of resolution may be used to simulate a region 770 around less significant features of an object 775 while the highest level of resolution is used to simulate regions 780 around the most significant features (e.g., the leading and trailing surfaces) of the object 775. Outlying regions 785 are simulated using the lowest level of resolution and the largest voxels.

Identify Voxels Affected by Facets

Referring again to FIG. 11, once the simulation space has been modeled (step 302), voxels affected by one or more facets are identified (step 304). Voxels may be affected by facets in a number of ways. First, a voxel that is intersected by one or more facets is affected in that the voxel has a reduced volume relative to non-intersected voxels. This occurs because a facet, and material underlying the surface represented by the facet, occupies a portion of the voxel. A fractional factor $P_f(x)$ indicates the portion of the voxel that is unaffected by the facet (i.e., the portion that can be occupied by a fluid or other materials for which flow is being simulated). For non-intersected voxels, $P_f(x)$ equals one.

Voxels that interact with one or more facets by transferring particles to the facet or receiving particles from the facet are also identified as voxels affected by the facets. All voxels that are intersected by a facet will include at least one state that receives particles from the facet and at least one state that transfers particles to the facet. In most cases, additional voxels also will include such states.

Figure 16:
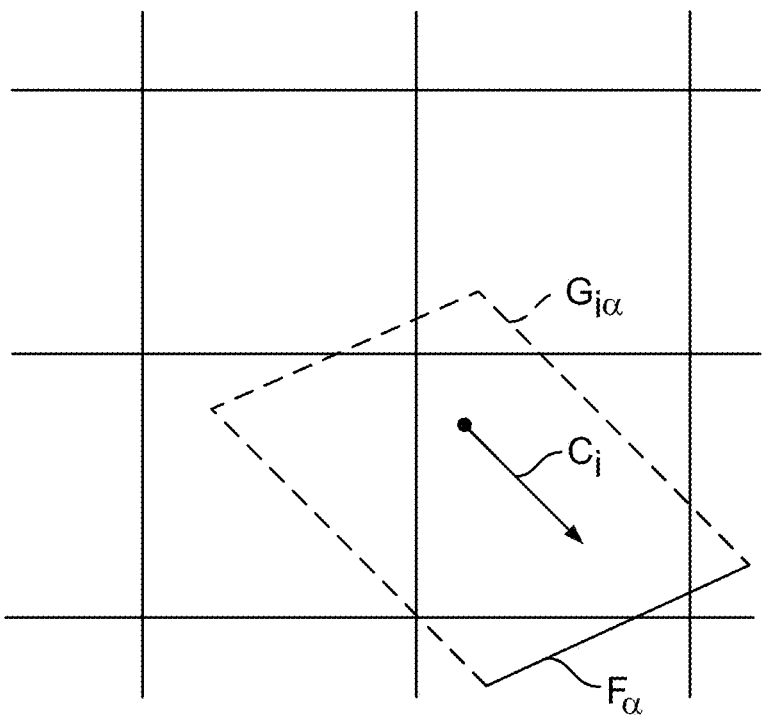
FIG. 16 illustrates regions affected by a facet of a surface (prior art).

Referring to FIG. 16, for each state i having a non-zero velocity vector $c_i$, a facet $F_\alpha$ receives particles from, or transfers particles to, a region defined by a parallelepiped $G_{i\alpha}$ having a height defined by the magnitude of the vector dot product of the velocity vector $c_i$ and the unit normal $n_\alpha$ of the facet ($|c_i n_\alpha|$) and a base defined by the surface area $A_\alpha$ of the facet so that the volume $V_{i\alpha}$ of the parallelepiped $G_{i\alpha}$ equals:

$$V_{i\alpha} = |c_i n_\alpha| A_\alpha \qquad \text{Eq.(I-6)}$$

The facet $F_\alpha$ receives particles from the volume $V_{i\alpha}$ when the velocity vector of the state is directed toward the facet ($|c_i n_\alpha| < 0$), and transfers particles to the region when the velocity vector of the state is directed away from the facet ($|c_i n_\alpha| > 0$). As will be discussed below, this expression must be modified when another facet occupies a portion of the parallelepiped $G_{i\alpha}$, a condition that could occur in the vicinity of non-convex features such as interior corners.

The parallelepiped $G_{i\alpha}$ of a facet $F_\alpha$ may overlap portions or all of multiple voxels. The number of voxels or portions thereof is dependent on the size of the facet relative to the size of the voxels, the energy of the state, and the orientation of the facet relative to the lattice structure. The number of affected voxels increases with the size of the facet. Accordingly, the size of the facet, as noted above, is typically selected to be on the order of or smaller than the size of the voxels located near the facet.

The portion of a voxel $N(x)$ overlapped by a parallelepiped $G_{i\alpha}$ is defined as $V_{i\alpha}(x)$. Using this term, the flux $\Gamma_{i\alpha}(x)$ of state i particles that move between a voxel $N(x)$ and a facet $F_\alpha$ equals the density of state i particles in the voxel ($N_i(x)$) multiplied by the volume of the region of overlap with the voxel ($V_{i\alpha}(x)$):

$$\Gamma_{i\alpha}(x) = N_i(x) V_{i\alpha}(x). \qquad \text{Eq.(I-7)}$$

When the parallelepiped $G_{i\alpha}$ is intersected by one or more facets, the following condition is true:

$$V_{i\alpha} = \Sigma V_{i\alpha}(x) + \Sigma V_{i\alpha}(\beta) \qquad \text{Eq.(I-8)}$$

where the first summation accounts for all voxels overlapped by $G_{i\alpha}$ and the second term accounts for all facets that intersect $G_{i\alpha}$. When the parallelepiped $G_{i\alpha}$ is not intersected by another facet, this expression reduces to:

$$V_{i\alpha} = \Sigma V_{i\alpha}(x). \qquad \text{Eq.(I-9)}$$

Perform Simulation

Once the voxels that are affected by one or more facets are identified (step 304), a timer is initialized to begin the simulation (step 306). During each time increment of the simulation, movement of particles from voxel to voxel is simulated by an advection stage (steps 308-316) that accounts for interactions of the particles with surface facets. Next, a collision stage (step 318) simulates the interaction of particles within each voxel. Thereafter, the timer is incremented (step 320). If the incremented timer does not indicate that the simulation is complete (step 322), the advection and collision stages (steps 308-320) are repeated. If the incremented timer indicates that the simulation is complete (step 322), results of the simulation are stored and/or displayed (step 324).

Figure 17A:
FIGS. 17A and 17B are diagrams that depict simulated coughs with placement of a boundary condition outside of the mouth and inside of the mouth (prior art).
Figure 17B:

FIGS. 17A and 17B depict a simulated cough jet with placement of boundary condition outside of the mouth (FIG. 17A) and inside of the mouth (FIG. 17B). In FIG. 17A, the cough jet does not sufficient deflect downward and does not disperse correctly, consistent with to experimental observations. In FIG. 17B, the cough jet improves over FIG. 17A, but still does not sufficient deflect downward and does not disperse correctly, according to experimental observations.

Figure 18:
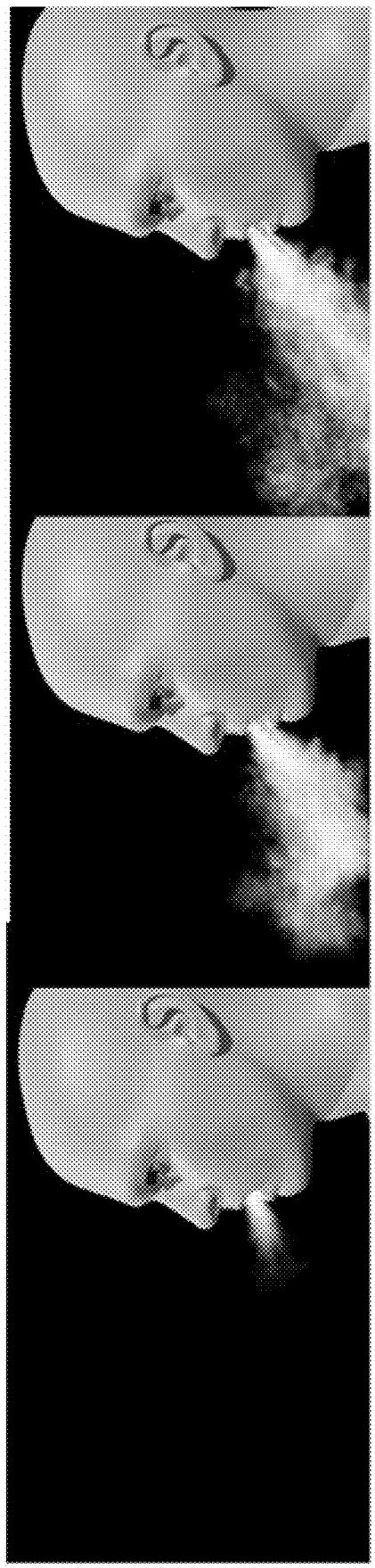
FIG. 18 is a diagram that depicts a simulated cough with placement of a boundary condition at an exit of the oropharynx.

FIG. 18 depicts a simulated cough jet with placement of the boundary condition at an exit of the oropharynx. In FIG. 18, the cough jet is now deflected downwards, agreeing with experimental observations, and angles for the cough cloud are now correct as also shown in FIG. 19B. The flow angle, velocity and momentum of both the case phase and particle phase exiting the mouth are available for post-processing.

Figure 19A:
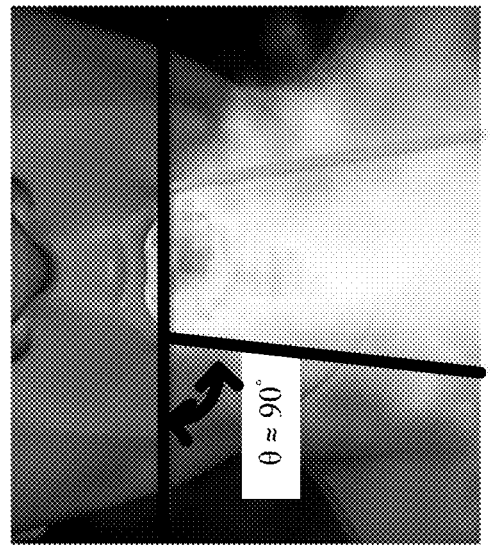
FIGS. 19A, 19B are diagrams that depict cough cloud details pertaining to the placement of boundary condition at the exit of the oropharynx of FIG. 18.
Figure 19A:
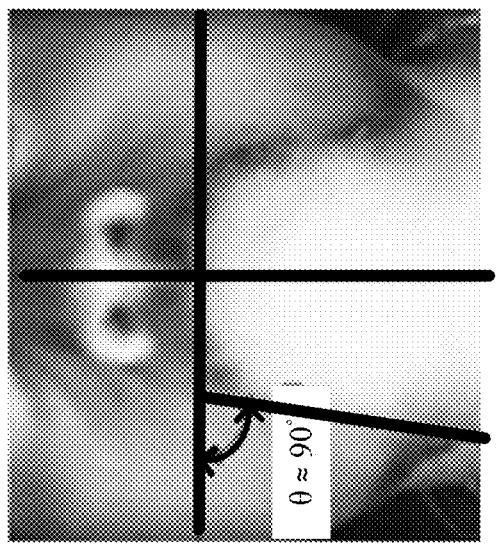
Figure 19B:
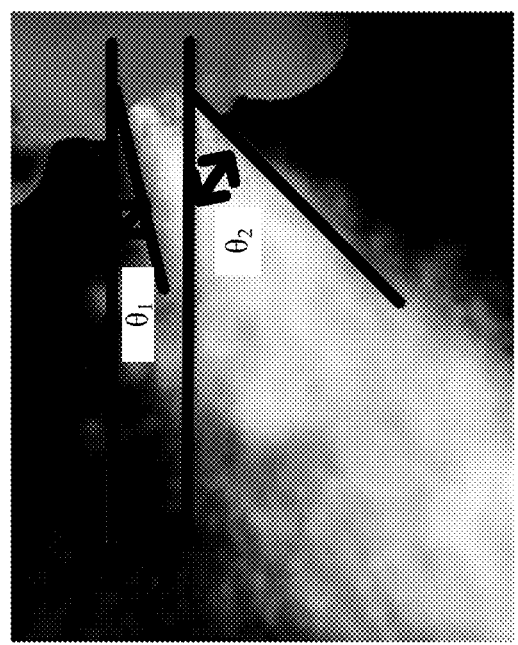
Figure 19B:
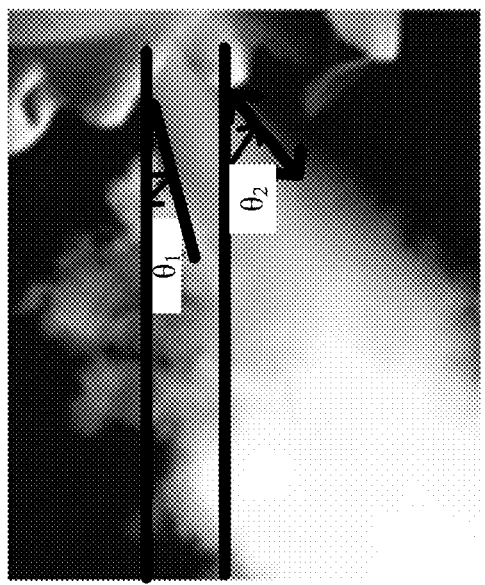

FIG. 19A is a diagram that depict cough jet side and front views pertaining to placement of boundary condition at the exit of the mouth FIG. 17A.

FIG. 19B is a diagram that depicts cough jet side and front views pertaining to the placement of boundary condition at the oropharynx region of the pharynx, as in FIG. 17B (similar to FIG. 7, but with angles depicted).

Embodiments of the subject matter and the functional operations described in this specification can be implemented in digital electronic circuitry, tangibly-embodied computer to software or firmware, computer hardware (including the structures disclosed in this specification and their structural equivalents), or in combinations of one or more of them. Embodiments of the subject matter described in this specification can be implemented as one or more computer programs (i.e., one or more modules of computer program instructions encoded on a tangible non-transitory program carrier for execution by, or to control the operation of, data processing apparatus). The computer storage medium can be a machine-readable storage device, a machine-readable storage substrate, a random or serial access memory device, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document, in a single file dedicated to the program in question, or in multiple coordinated files (e.g., files that store one or more modules, sub-programs, or portions of code)). A computer program can be deployed so that the program is executed on one computer or on multiple computers that are located at one site or distributed across multiple sites and interconnected by a data communication network.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data (e.g., magnetic, magneto-optical disks, or optical disks), however, a computer need not have such devices.

Computer-readable media suitable for storing computer program instructions and data include all forms of non-volatile memory on media and memory devices, including by way of example semiconductor memory devices (e.g., EPROM, EEPROM, and flash memory devices), magnetic disks (e.g., internal hard disks or removable disks), magneto-optical disks, and CD-ROM and DVD-ROM disks. The processor and the memory can be supplemented by, or incorporated in, special purpose logic circuitry.

What is claimed is:

1. A method performed by one or more computer systems to simulate a respiratory event, the method comprising:
    digitally processing, by one or more computer systems, one or more images of a person's respiratory tract to identify one or more objects in the person's respiratory tract to be modeled;
    generating, by the one or more computer systems, a model including a portion of the person's respiratory tract based on the one or more objects identified by digitally processing the one or more images, wherein the respiratory tract is represented as a volumetric region comprising a plurality of voxels, wherein a resolution level of the model is higher for one or more regions of interest in the model than for one or more regions of the model outside of the one or more regions of interest;
    initiating a respiratory event into the volumetric region, by:
        simulating, by the one or more computer systems, a cough in the volumetric region, which simulated cough originates in the generated model at a depth that is inside of the modeled respiratory tract;
    simulating, by the one or more computer systems, movement of elements of the respiratory event within the volumetric region, with the elements representing particles of the respiratory event, at an inlet boundary condition, with the inlet boundary condition occurring at one or more voxels representing an oropharynx region or a laryngopharynx region of the person's respiratory tract;
    obtaining, by the one or more computer systems, from the simulating, a visual representation of a trajectory of particles of the respiratory event; and
    displaying, by the one or more computers systems, on a display device the visual representation including the simulated movement of particles of the respiratory event within the volumetric region, including:
        displaying in a user interface one or more regions of the visual representation corresponding to the one or more regions of interest in the model with a higher resolution level than one or more regions of the visual representation corresponding to the one or more regions of the model outside of the one or more regions of interest.

2. The method of claim 1 wherein the representation of the respiratory tract includes a model of the pharynx.

3. The method of claim 2 wherein the representation of the respiratory tract includes a model of the oropharynx region of the pharynx.

4. The method of claim 1 wherein initiating occurs at a region that represents the oropharynx region of the pharynx, with simulating further comprising:
    simulating fluid flow of the respiratory event from the oropharynx region of the pharynx through the oral cavity and out of the mouth of a person.

5. The method of claim 1 wherein initiating occurs at a region that represents the laryngopharynx region of the pharynx, with simulating further comprising:
    simulating fluid flow of the respiratory event from the laryngopharynx region of the pharynx through the oropharynx region, the oral cavity, and out of the mouth of a person.

6. A computer system comprises:
    one or more processor devices;
    memory coupled to the one or more processor devices;
    storage media storing executable computer instructions for simulating a human respiratory event, the instructions to configure the one or more processors to:
    digitally process one or more images of a person's respiratory tract to identify one or more objects in the person's respiratory tract to be modeled;
    generate a model including a portion of the person's respiratory tract based on the one or more objects identified by digitally processing the one or more images, which models the respiratory tract as a volumetric region comprising a plurality of voxels, wherein a resolution level of the model is higher for one or more regions of interest in the model than for one or more regions of the model outside of the one or more regions of interest;
    initiate a respiratory event into the volumetric region, by:
        simulating a cough in the volumetric region, which simulated cough originates in the generated model at a depth that is inside of the modeled respiratory tract;
    simulate movement of elements of the respiratory event within the volumetric region, with the elements representing particles of the respiratory event, at an inlet boundary condition, with the inlet boundary condition occurring at one or more voxels representing an oropharynx region or a laryngopharynx region of the person's respiratory tract;

obtain from the simulation, a visual representation of a trajectory of particles of the respiratory event; and display on a display device the visual representation including the simulated movement of particles of the respiratory event within the volumetric region, including:

displaying in a user interface one or more regions of the visual representation corresponding to the one or more regions of interest in the model with a higher resolution level than one or more regions of the visual representation corresponding to the one or more regions of the model outside of the one or more regions of interest.

7. The system of claim 6 wherein the representation of the respiratory tract includes a model of the pharynx.

8. The system of claim 7 wherein the representation of the respiratory tract includes a model of the oropharynx region of the pharynx.

9. The system of claim 6 wherein the system is further configured to:

initiate the respiratory event at a region that represents the oropharynx region of the pharynx, with the system further configured to:

simulate fluid flow of the respiratory event from the oropharynx region of the pharynx through the oral cavity and out of the mouth of a person.

10. The system of claim 6 wherein the system is further configured to:

initiate at a region that represents the laryngopharynx region of the pharynx, with the system further configured to:

simulate fluid flow of the respiratory event from the laryngopharynx region of the pharynx through the oropharynx region, the oral cavity, and out of the mouth of a person.

11. A computer program product tangibly stored on a computer readable non-transitory storage device that stores executable computer instructions to simulate a human respiratory event, the instructions for causing a computing system to:

digitally process one or more images of a person's respiratory tract to identify one or more objects in the person's respiratory tract to be modeled;

generate a model including a portion of the person's respiratory tract based on the one or more objects identified by digitally processing the one or more images, wherein the respiratory tract is represented as a volumetric region comprising a plurality of voxels, wherein a resolution level of the model is higher for one or more regions of interest in the model than for one or more regions of the model outside of the one or more regions of interest;

initiate a respiratory event into the volumetric region, by:

simulating a cough in the volumetric region, which simulated cough originates in the generated model at a depth that is inside of the modeled respiratory tract;

simulate movement of elements of the respiratory event within the volumetric region, with the elements representing particles of the respiratory event, at an inlet boundary condition, with the inlet boundary condition occurring at one or more voxels representing an oropharynx region or a laryngopharynx region of the person's respiratory tract;

obtain from the simulation, a visual representation of a trajectory of particles of the respiratory event; and display on a display device the visual representation including the simulated movement of particles of the respiratory event within the volumetric region, including:

displaying in a user interface one or more regions of the visual representation corresponding to the one or more regions of interest in the model with a higher resolution level than one or more regions of the visual representation corresponding to the one or more regions of the model outside of the one or more regions of interest.

12. The computer program product of claim 11 wherein the representation of the respiratory tract includes a model of the pharynx.

13. The computer program product of claim 12 wherein the representation of the respiratory tract includes a model of the oropharynx region of the pharynx.

14. The computer program product of claim 11 wherein instructions to initiate occur at a region that represents the oropharynx region of the pharynx, with the instructions further comprising instructions to:

simulate fluid flow of the respiratory event from the oropharynx region of the pharynx through the oral cavity and out of the mouth of a person.

15. The computer program product of claim 11 wherein the instructions further comprise instructions to:

initiate at a region that represents the laryngopharynx region of the pharynx, with instructions to simulate further comprising instructions to:

simulate fluid flow of the respiratory event from the laryngopharynx region of the pharynx through the oropharynx region, the oral cavity, and out of the mouth of a person.

16. The method of claim 1, wherein the simulated cough is based on a combination of exhalation rate profiles, particle distribution sizes, and concentration data.

17. The method of claim 1, wherein the model comprising one or more smaller voxels in the one or more regions of interest and one or more larger voxels in the one or more regions outside the one or more regions of interest improves a processing efficiency of initiating the respiratory event by the one or more computers and simulating movement of the elements by the one or more computer systems relative to a model comprising uniformly sized voxels.

* * * * *